(12) United States Patent
Akashi et al.

(10) Patent No.: US 8,389,686 B2
(45) Date of Patent: Mar. 5, 2013

(54) NONCOVALENT COLLAGEN CROSSLINKING AGENT

(75) Inventors: Mitsuru Akashi, Suita (JP); Kohji Nishida, Sendai (JP); Michiya Matsusaki, Suita (JP); Akira Kubota, Sendai (JP); Tomonori Waku, Suita (JP)

(73) Assignees: Osaka University, Osaka (JP); Tohoku University, Miyagi (JP)

( * ) Notice: Subject to any disclaimer, the term of this patent is extended or adjusted under 35 U.S.C. 154(b) by 144 days.

(21) Appl. No.: 12/990,897

(22) PCT Filed: May 1, 2009

(86) PCT No.: PCT/JP2009/058554
§ 371 (c)(1),
(2), (4) Date: Nov. 22, 2010

(87) PCT Pub. No.: WO2009/136599
PCT Pub. Date: Nov. 12, 2009

(65) Prior Publication Data
US 2011/0060129 A1 Mar. 10, 2011

(30) Foreign Application Priority Data
May 7, 2008 (JP) .................. 2008-121073

(51) Int. Cl.
*C07K 14/78* (2006.01)
*A61K 38/00* (2006.01)
(52) U.S. Cl. ...................... 530/356; 530/300
(58) Field of Classification Search ............. 530/356, 530/300
See application file for complete search history.

(56) References Cited

U.S. PATENT DOCUMENTS
2003/0162941 A1 8/2003 Tanihara et al.

FOREIGN PATENT DOCUMENTS

| | | | |
|---|---|---|---|
| JP | 2003-522150 A | 7/2003 | |
| JP | 2003-321500 A | 11/2003 | |
| JP | 2004-536107 A | 12/2004 | |
| JP | 2005-526793 A | 9/2005 | |
| WO | WO 01-58461 A1 | 8/2001 | |
| WO | WO 03/004055 A2 | 1/2003 | |
| WO | WO 03/080114 A2 | 10/2003 | |
| WO | WO 2006/058215 A2 | 6/2006 | |
| WO | 2007-112924 A | 5/2007 | |
| WO | WO 2007/120457 A2 | 10/2007 | |

OTHER PUBLICATIONS

Amekawa, Ryotaro et al., "PEG-Collagen Model Peptide (Pro-Hyp-Gyl) ni yoru Collagen no Tokuiteki Gel-kano Hyoka," P3-89, Japanese Society for Biomaterials Symposium, vol. 2008, p. 381, Nov. 17, 2008.
Amekawa, Ryotaro et al., "Sanju Rasen Keisei ni yori Collagen o Tokuiteki ni Kakyo suru Seitai Tekigosei Gel-kazai no Chosei," 2Pa171, Polymer Preprints, vol. 57, No. 1, p. 1908, May 8, 2008.
International Search Report dated Aug. 11, 2009 in Application No. PCT/JP2009/058554.
Murakami, Yoshihiko et al., "A novel synthetic tissue-adhesive hydrogel using a crosslinkable polymeric micelle," J. Biomed. Mater. Res. 80A, pp. 421-427, 2007.
Nakayama, Yasuhide et al., "Photocurable Surgical Tissue Adhesive Glues Composed of Photoreactive Gelatin and Poly(ethylene glycol) Diacrylate," J. Biomed. Mater. Res. (Appl. Biomater.), vol. 48, pp. 511-521, 1999.
Taguchi, Tetsushi et al., "Bonding of soft tissues using a novel tissue adhesive consisting of a citric acid derivative and collagen," Materials Science and Engineering C, vol. 24, pp. 775-780, 2004.
Wallace, D.G. et al., "A Tissue Sealant Based on Reactive Multifunctional Polyethylene Glycol," J. Biomed. Mater. Res. (Appl. Biomater.), vol. 58, pp. 545-555, 2001.
Wollensak, Gregor et al., "Riboflavin/Ultraviolet-A-induced Collagen Crosslinking for the Treatment of Keratoconus," Am. J. Opthalmol., vol. 135, pp. 620-627, 2003.
Extended European Search Report issued in European Patent Application No. 09742723.1 on May 9, 2012.
Thomson Scientific Database WPI Week 200742. XP-002675001, (2007).

*Primary Examiner* — Chih-Min Kam
(74) *Attorney, Agent, or Firm* — Birch, Stewart, Kolasch & Birch, LLP

(57) ABSTRACT

The present invention provides a collagen crosslinking agent superior in biocompatibility that is free from the damage by UV irradiation and also from the problems of toxicity caused by residual monomer or unreacted functional groups. Provided is a noncovalent collagen crosslinking agent (for fibrous protein collagen), comprising a spacer of a polyvalent alcohol having two or more OH groups at the terminals and arms of collagen peptides formed of repetitions of three amino acids, the arms being bound via the OH groups to the spacer.

7 Claims, 4 Drawing Sheets

NONCOVALENT COLLAGEN CROSSLINKING AGENT

This application is a national stage application under 35 U.S.C.§371 of application No. PCT/JP2009/058554, filed May 1, 2009, which claims priority under 35 U.S.C.§119 to Japanese application No. 2008-121073, filed May 7, 2008.

TECHNICAL FIELD

The present invention relates to a collagen crosslinking agent, in particular to a noncovalent collagen crosslinking agent.

BACKGROUND ART

Conical cornea is a disease that a corneal parenchymal layer thins and a central region protrudes. Its reason is not yet understood and there is currently no treatment method other than suppression of the protrusion with a contact lens or transplantation of cornea.

In a study for treatment of conical cornea, there is reported a method of crosslinking collagen in the corneal parenchymal layer by adding riboflavin (vitamin B2) dropwise into the eye and irradiating the eye with ultraviolet ray (for example, Non-patent Document 1). However, it is difficult to stop progress of conical cornea completely and the damage due to UV irradiation also causes a problem.

Crosslinking agents that crosslink collagen by chemical bondings are known. For example, known in Japan are a photoreactive gelatin-polyethylene glycol (PEG) diacrylate crosslinking agent, developed by Matsuda et al. (Non-patent Document 2), a succinimidated citric acid crosslinking agents, developed by Taguchi et al. (Non-patent Document 3) and an aldehyde group-containing polymeric micelle crosslinking agent, developed by Murakami et al. (Non-patent Document 4); and known abroad are succinimidated PEGs, developed by Wallance et al. (Non-patent Document 5) and others. However, there is concern about toxicity by residual monomers and unreacted functional groups and there is also a problem of stability.

Patent Document

[Non-patent Document 1] T. Seiler et al., Am. J. Ophthalmol., 135, 620 (2003)
  [Non-patent Document 2] J. Biomed. Mater. Res. 1999
  [Non-patent Document 3] Mater. Sci. Eng. C2004
  [Non-patent Document 4] J. Biomed. Mater. Res. 2007
  [Non-patent Document 5] J. Biomed. Mater. Res. 2001

DISCLOSURE OF INVENTION

Technical Problems to be Solved

The present inventions were made under the circumstances above. An object of the present invention is to provide a collagen crosslinking agent superior in biocompatibility that is free from bad influences by UV irradiation and also from problems of toxicity caused by residual monomers or unreacted functional groups.

Means to Solve the Problems

The present invention provides a noncovalent collagen crosslinking agent, comprising a spacer of a polyvalent alcohol having two or more OH groups at terminals and arms of collagen peptides formed of repetitions of three amino acids, the arms being bound to the spacer via the OH groups.

Effect of the Invention

The crosslinking agent according to the present invention is superior in biocompatibility and the driving force thereof for crosslinking is caused from formation of triple helix. Thus, there is no need for UV irradiation, and there is no concern about adverse reactions caused by UV irradiation, even if the crosslinking agent according to the present invention is administered to the body. There is also no concern about generation of toxicity caused by residual monomers or reactive functional groups, its problem being associated with conventional chemical crosslinking agents.

BEST MODE FOR CARRYING OUT THE INVENTION

Figure 1:
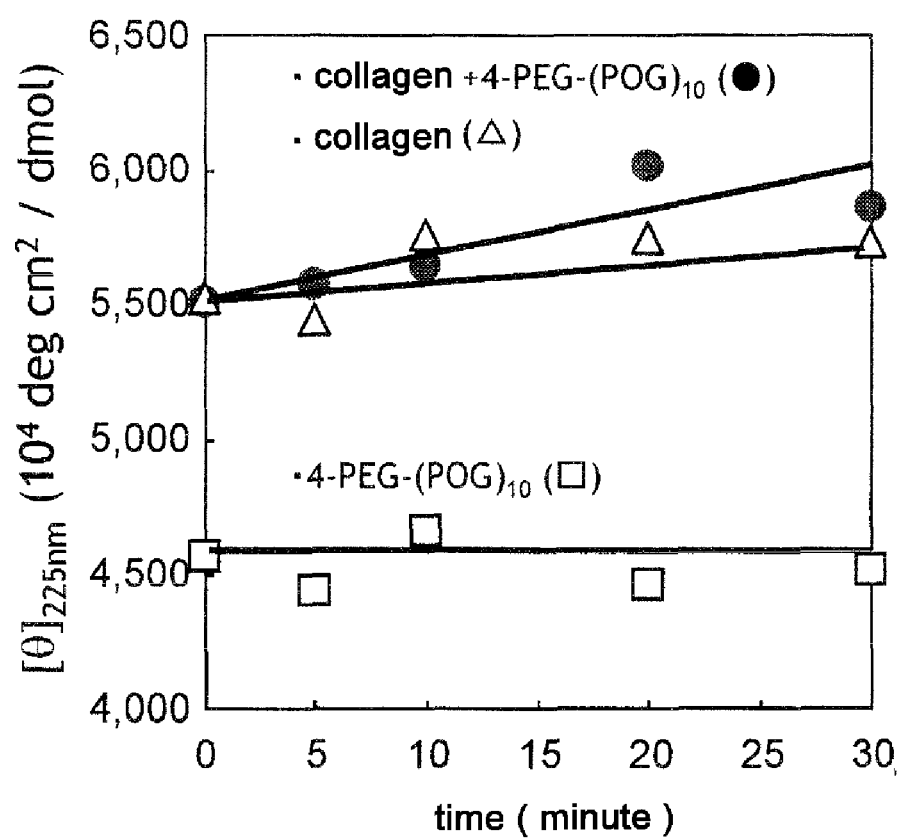
FIG. 1 is a graph showing a change with time of $[\theta]_{225nm}$ in CD spectra of a crosslinking agent according to the present invention and collagen.

The collagen crosslinking agent according to the present invention has a spacer and arms extending from the spacer.

The spacer, which has a role to control the distance between arms and provide hydrophilicity, is a base for connection with the arms described below. Specifically, it is a multiply branching polyvalent alcohol having two or more OH groups at the terminals.

Two or more OH groups may be present at the terminals. The term "terminal" above means that the compound may have OH groups at positions other than the terminals of branching chains, but such OH groups are not included in the number of OH groups specified in the present invention. Only terminal OH groups are included, for the purpose of controlling the distance between arms.

Although the maximum number of the OH groups is not particularly limited, from the viewpoints of solubility and steric repulsion of the arms is a polyvalent alcohol having 2 to 512 OH groups, preferably 3 to 16 OH groups, more preferably 4 to 16 OH groups, and still more preferably 4 to 8 OH groups, and particularly 4 OH groups.

Specific examples of the polyvalent alcohols having two or more OH groups at the terminals include bivalent alcohols such as ethylene glycol, propylene glycol, butylene glycol, diethylene glycol, erythritol, threitol, ribitol, xylitol, mannitol, catechol, catechin and bisphenol A; trivalent alcohols such as glycerol and trihydroxybenzene; tetravalent alcohols such as pentaerythritol, diglycerin, pentaerythritol polyethylene glycol ether, for example, pentaerythritol tetrapolyethylene glycol ether; hexavalent alcohols such as dipentaerythritol and inositol; octavalent alcohols such as hexaglycerol polyethylene glycol ether, for example, hexaglycerol octapolyethylene glycol ether; 16-valent alcohols such as hydroxylated polyamide amine dendrimer (generation number: 2); 32-valent alcohols such as hydroxylated polyamide amine dendrimer (generation number: 3); 64-valent alcohols such as hydroxylated polyamide amine dendrimer (generation number: 4); 128-valent alcohols such as hydroxylated polyamide amine dendrimer (generation number: 5); 256-valent alcohols such as hydroxylated polyamide amine dendrimer (generation number: 6); 512-valent alcohols such as hydroxylated polyamide amine dendrimer (generation number: 7); monosaccharides such as glucose, fructose and galactose; disaccharides and the oligosaccharides and polysaccharides thereof.

From the viewpoint of biological safety, the arms may be extended, for example, with an alkylene glycol or a polyalkyleneoxide such as polyethylene glycol, polypropylene glycol or polyethyleneoxide, and the OH groups of the polyvalent alcohol are given at chain-extended terminals as terminal OH groups (hereinafter, the chain-extended alcohol may be referred to as "chain-extended polyvalent alcohol", and in the present invention, such chain-extended polyvalent alcohols are also included in the "polyvalent alcohols").

From the viewpoint of crosslinking, the polyvalent alcohol may be soluble in solution, in an amount of about 0.1 to 500 mg (0.01 to 50 wt %) in 1 ml of the solution. A high-molecular weight polyvalent alcohol can also be used, if it satisfies the conditions above, and the molecular weight thereof is not limited.

Among the polyvalent alcohols, the ones containing much a biological component or a compound or component superior in biocompatibility are used preferably for improvement of biological safety.

Examples of such polyvalent alcohols include bivalent alcohols such as polyethylene glycol, polypropylene glycol, polyethyleneoxide, erythritol, threitol, ribitol, xylitol, mannitol, catechol and catechin; trivalent alcohols such as glycerol; tetravalent alcohols such as pentaerythritol, diglycerin and pentaerythritol polyethylene glycol ether; hexavalent alcohols such as dipentaerythritol and inositol; octavalent alcohols such as hexaglycerol polyethylene glycol ether; monosaccharides such as glucose, fructose and galactose; disaccharides and oligosaccharides and polysaccharides thereof.

Polyvalent alcohol preferably used in the present invention may be selected from the viewpoints of the number of terminal OH groups, hydrophilicity and biological safety, but should be selected properly with steric repulsion by arms and distance between arms taken into consideration. It is preferable, however, to have three or more arms, in order to obtain a collagen gel having a sufficiently high mechanical strength and thus, the polyvalent alcohol for use is preferably a trivalent or higher alcohol.

All of the polyvalent alcohols above are commercially available and can be prepared by those who are skilled in the art.

The arm is constituted of a collagen peptide or a collagen model peptide, formed of repetitions of three amino acids. The collagen model peptide means a peptide formed of repetitions of amino acids similar to collagen peptide. The arms form triple helix with collagen molecules, crosslinking the collagen molecules. The arms, which are made of amino acids, are superior in biocompatibility.

The arm is represented by the following General Formula (I) having peptide bonds:

$$(Y-X-G)_n \qquad (I)$$

wherein, G represents glycine (Gly) residue; X and Y each independently represent an amino acid residue such as alanine (Ala) residue (A), proline (Pro) residue (P), hydroxyproline (Hyp) residue (O), and glycine (Gly) residue (G), preferably alanine (Ala) residue (A), proline (Pro) residue (P) or hydroxyproline (Hyp) residue (O), particularly preferably proline (Pro) residue (P) or hydroxyproline (Hyp) residue (O). X and Y may be chemically modified with a methyl group, an isobutyl group or a fluorine atom, and examples of such groups include N-isobutyl glycine, N-methyl alanine, and 4-fluoroproline. The word of n is an integer of 1 to 50, preferably of 5 to 20.

Preferable (Y—X-G) is (P—O-G), (P—P-G), (P-A-G), (P—N-isobutyl glycine (Nleu)-G), (P—N-methylalanine (meA)-G) or (P-fluoroproline (Flp)-G), more preferably (P—O-G), (P—P-G) or (P-A-G), and still more preferably (P—O-G) from the viewpoint of the stability of triple helix.

The arm represented by the Formula above can be prepared by those who are skilled in the art, for example by liquid-phase peptide synthesis method, solid-phase peptide synthesis method or genetic engineering method. For example, (P—O-G)$_{10}$ can be prepared by solid-phase peptide synthesis method. In addition, (P—O-G)$_{10}$ is also available commercially under the trade name of (Pro-Hyp-Gly)$_{10}$-20H$_2$O from Peptide Institute, Inc.

The arm is bound to the spacer. The bonding form changes, depending on whether the carboxyl group (COOH) terminal or the amino group (>NH or NH$_2$) terminal of the arm is used.

When the carboxyl group terminal of the arm is used, the arm and the spacer are bound to each other, via ester bonds formed between the carboxyl group (COOH) thereof and the OH groups of the spacer. Such an ester bond-forming reaction may be carried out by a method commonly used, such as an active esterification method of carboxyl groups or a method of using a condensing agent.

When the amino group-terminal of the arm is used, it is difficult to form a bond by direct reaction of the amino groups of the arm with the hydroxyl groups of the spacer. Therefore, the arm and the spacer may be bound to each other by using an amide bond-forming reaction, for example, by chemically modifying the spacer terminals to form N-hydroxysuccinimide-ester for coupling reaction. Alternatively, the arm and the spacer may be bound to each other, by esterification of the spacer terminal OH group, such as mesylation, tosylation, or para-nitrophenyl esterification.

It is not needed to make the arm bound to all OH groups of the spacer, and the terminal OH groups of at least two spacers are bound to the arms. Increase in the number of spacer-arm bonds leads to increase of crosslinking points during crosslinking of the collagen molecules. The number of the arms bound to the spacer may be adjusted properly depending on application, desirable crosslinking strength or the like.

A commercially available product may be used as the spacer. Examples of bivalent alcohol spacers for use include 2-arm type polyethylene glycol (2-arm-PEG) (molecular weight (MW): 3000 to 20000) available as SUNBRIGHT DE series from NOF Corporation, 4-arm type polyethylene glycol (4-arm-PEG) (molecular weight (MW): 10000 to 20000) available as SUNBRIGHT PTE series from NOF Corporation, and 8-arm type polyethylene glycol (8-arm-PEG) (molecular weight (MW): 20000) available as SUNBRIGHT HGEO series from NOF Corporation. The products in the above series are polyvalent alcohols previously esterified to N-hydroxysuccinimide-esters. Other commercially available terminal succinimide-esterified branching polyethylene glycol and others are also usable as the spacer for the crosslinking agent according to the present invention.

Particles such as gold particles may be used as the spacer. When gold particles are used, the Y terminal in General Formula (I) is bound to an amino acid having a —SH bond, such as cysteine residue. It is because Au—S bonds are formed with gold (Au), thus making it possible to bind the spacer with the arm. In the case of other particles (for example, polystyrene particles having carboxyl groups on the surface), an amino acid having a functional group that forms a bond with the particle (lysine in the case of the polystyrene particle) may be used as the Y terminal. The size of the particles is preferably as small as about 1 to 100 nm. The particle size is preferably smaller. Particle size of more than 100 nm may be larger than collagen fiber diameter, causing a problem of inhibiting mutual approach between collagen fibers.

The arm can be bound to the gold particles, for example by a method of incubation at room temperature.

When added to an aqueous collagen solution, the collagen crosslinking agent according to the present invention forms crosslinkages with the triple helix formation between the collagen crosslinking agent and the collagen molecules used as a driving force. The collagen molecules are then crosslinked through noncovalent bonds.

Formation of the triple helix between the collagen crosslinking agent and the collagen molecules can be confirmed by circular dichroism spectrum (CD spectrum) and also by collagen gel formation by mixing.

The collagen to which the collagen crosslinking agent according to the present invention is applicable is not particularly limited, and examples thereof include one of proteins constituting skin, ligaments, sinews, bones, cartilages, cornea, blood vessel, basal layers and internal organs, which is known as a major component of extracellular substrates (extracellular matrixes) of multicellular animals; collagens chemically treated, for example, with acid, alkali or enzyme; chemically-modified collagens and synthetic collagens. The collagen crosslinking agent according to the present invention can be used favorably for fibrous protein collagens among the collagens above.

How to use the collagen crosslinking agent according to the present invention and the collagen includes mixing both the aqueous solutions each other. A mixing ratio thereof may be determined properly according to applications for use, but is set to 1/100 to 1/1, preferably 1/10 to 1/2 (by weight) from the viewpoint of gel strength.

The collagen crosslinking agent according to the present invention, which can be constituted with biocompatible components, may be applicable to treatment, for example, of conical cornea, a disease of thinning and protruding of the cornea caused by deterioration of crosslinking of the collagen constituting the cornea.

EXAMPLES

Example 1

Synthesis of 4-arm-PEG-(POG)$_{10}$ (POG)$_{10}$ was introduced to the terminals of 4-arm-PEG, by treating succinimide-esterified 4-arm-PEG (NHS) and (POG)$_{10}$ (CMP) in condensation reaction in the amounts and the molar ratio shown in the Table below in 6 ml of sodium carbonate buffer (50 mM, pH: 8.2) in the presence of a condensing agent 1-ethyl-3-(3-dimethylaminopropyl)carbodiimide (WSC) and an auxiliary 1-hydroxybenzotriazole (HOBt) for 24 hours (see the following reaction formula).

The introduction rate of (POG)$_{10}$ was determined by $^1$H-NMR spectrum measurement, showing that the introduction rate of the POG chain was approximately 80%. The yield was 80% or more, indicating that the reaction proceeded almost quantitatively.

The succinimide-esterified 4-arm-PEG used was SUNBRIGHT PTE-100GS (product name) (MW: 10000, produced by NOF Corporation).

(POG)$_{10}$ means (Pro-Hyp-Gly)$_{10}$ and specifically, the product name (Pro-Hyp-Gly)$_{10}$-20H$_2$O (produced by Watanabe Chemical Industries, Ltd.) was used.

[Formula 1]

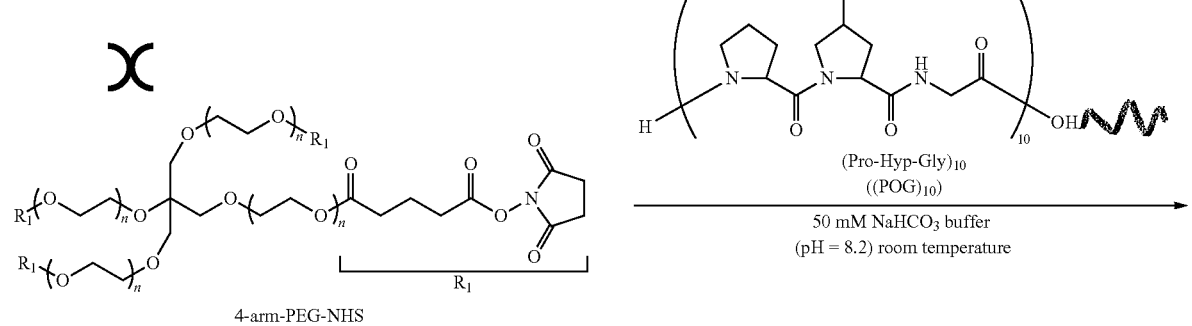

-continued

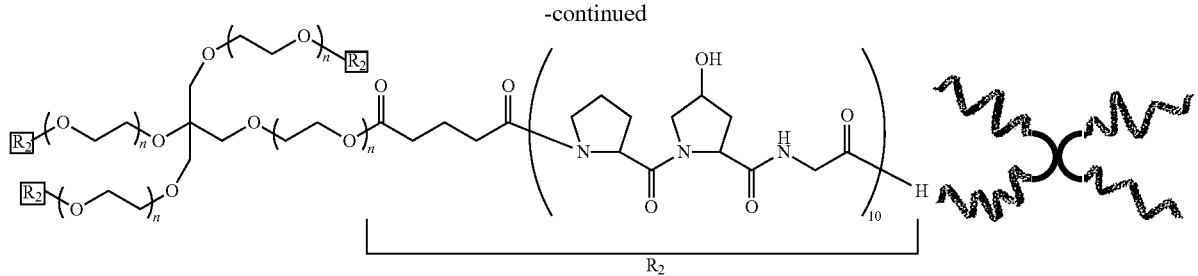

TABLE 1

| run No. | 4-arm-PEG-NHS (μmol) | (POG)$_{10}$ (μmol) | WSC (μmol) | HOBt (μmol) | molar ratio NHS:(POG)$_{10}$:WSC:HOBt | yield (%) | Introduction rate (%) |
|---|---|---|---|---|---|---|---|
| 1 | 4.1 | 16.4 | 0 | 0 | 1:1:0:0 | 77 | 67 |
| 2 | 4.1 | 16.4 | 32.8 | 32.8 | 1:1:2:2 | 87 | 80 |
| 3 | 8.2 | 32.8 | 65.6 | 65.6 | 1:1:2:2 | 82 | 81 |

Example 2

Synthesis of 2-arm-PEG-(POG)$_{10}$ (POG)$_{10}$ was introduced to the terminals of 2-arm-PEG by treating 8.2 μmol of succinimide-esterified 2-arm-PEG (NHS) and 16.4 μmol of (POG)$_{10}$ (CMP) in condensation reaction in 6 ml of sodium carbonate buffer (50 mM, pH: 8.2) in the presence of 32.8 μmol of WSC and HOBt for 24 hours.

The introduction rate of (POG)$_{10}$ was determined by $^1$H-NMR spectrum measurement, showing that the introduction rate of POG chain was approximately 80%. The yield was 90% or more, indicating that the reaction proceeded almost quantitatively.

Example 3

Synthesis of 8-arm-PEG-(POG)$_{10}$ (POG)$_{10}$ was introduced to the terminals of 8-arm-PEG by treating 2.1 μmol of succinimide-esterified 8-arm-PEG (NHS) and 16.4 μmol of (POG)$_{10}$ (CMP) in condensation reaction in 6 ml of sodium carbonate buffer (50 mM, pH: 8.2) in the presence of 32.8 mol of WSC and HOBt for 24 hours.

The introduction rate of (POG)$_{10}$ was determined by $^1$H-NMR spectrum measurement, showing that the introduction rate of POG chain was approximately 80%. The yield was 90%, indicating that the reaction proceeded almost quantitatively.

Confirmation of Formation of Triple Helix of 4-arm-PEG-(POG)$_{10}$ 2.2 mg of the 4-arm-PEG-(POG)$_{10}$ obtained (Run No. 2 in Table 1) was dissolved in 1 ml of 50 mM sodium carbonate buffer solution (pH: 8.2), and the mixture was diluted 100 times with sodium carbonate buffer, to give a 22 μg/ml solution. The concentration was so adjusted that the concentration of (POG)$_{10}$ became 10 μg/ml in the solution. CD spectrum measurement at 25° C. temperature confirmed presence of a positive peak at 225 nm. It is a peak due to the triple helix, indicating that 4-arm-PEG-(POG)$_{10}$ formed triple helix.

Confirmation of Formation of Triple Helix by 4-arm-PEG-(POG)$_{10}$ and Collagen 10 mg of porcine skin-derived type-I atelocollagen (manufactured by Nippon Meat Packers, Inc.) was dissolved in 1 ml of 50 mM sodium carbonate buffer solution (pH: 8.2), and the mixture was diluted 1000 times with sodium carbonate buffer, to give a 10 μg/ml solution. The 22 μg/ml 4-arm-PEG-(POG)$_{10}$ solution thus prepared (Run No. 2 in Table 1) and the collagen solution were mixed with each other in the same amount and the CD spectrum ($[\theta]_{225nm}$) and the change ($[\theta]_{225nm}$) thereof were measured. Results are shown in FIG. 1.

FIG. 1 shows variation with time of $[\theta]_{225nm}$ after mixing of the crosslinking agent and collagen (temperature: 25° C.). FIG. 1 additionally shows the results for comparison obtained by measurement by using only 4-arm-PEG-(POG)$_{10}$ or collagen used above.

The results shown in FIG. 1 demonstrate that addition of the 4-arm-PEG-(POG)$_{10}$ to collagen lead to increase of $\theta_{225}$, indicating that triple helix was formed by the collagen and the crosslinking agent.

Collagen Gelation Ability 1 ml of a solution containing 4-arm-PEG-(POG)$_{10}$ (Run No. 2 in Table 1) dissolved in an acetate buffer solution at a concentration of 20 wt % was mixed with 0.1 ml of a 10 wt % aqueous solution of porcine type-I collagen, to give a collagen/acetate buffer solution. A gel was formed within 1 minute.

The 2-arm-PEG-(POG)$_{10}$ and the 8-arm-PEG-(POG)$_{10}$ prepared in Examples 2 and 3 were mixed with collagen in a manner similar to the above. Gels were also formed.

Such gel formation indicates that 2-, 4- or 8-arm-PEG-(POG)$_{10}$ forms triple helix with collagen molecules, resulting in crosslinking collagen molecules with each other.

The gel obtained was stable and transparent, and the results suggest a possibility to application to the ophthalmic field for treatment of conical cornea.

Dynamic Viscoelasticity

Figure 2:
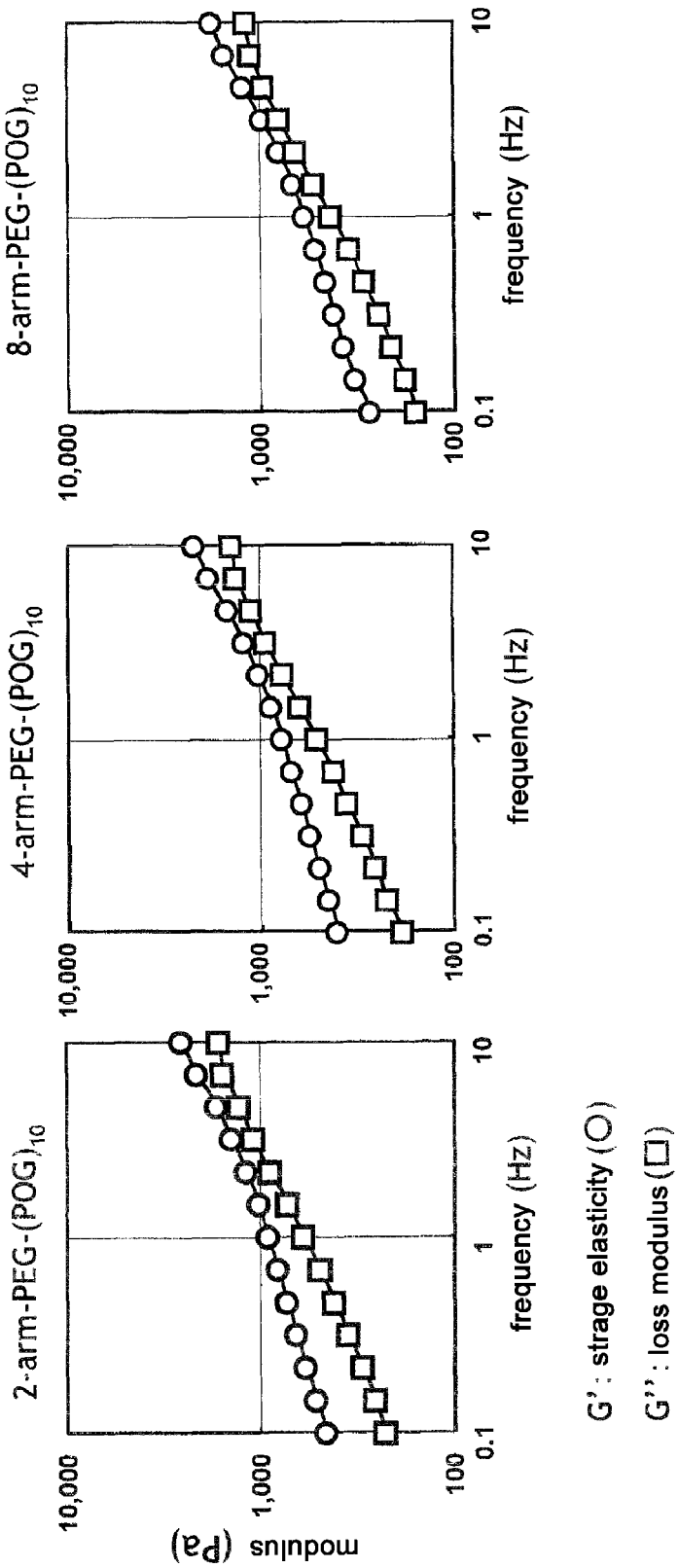
FIG. 2 includes graphs showing dynamic viscoelasticity of gel formed from the crosslinking agent according to the present invention and collagen.

The dynamic viscoelasticity of the collagen gels with 2-, 4- or 8-arm-PEG-(POG)$_{10}$ obtained in the test for collagen gelation ability was measured. In measurement, storage modulus and loss modulus were determined, by placing the gel over the entire sampling face and the pressurizing face at a position 0.5 mm above the gel surface and then starting the measurement. Results are shown in FIG. 2.

Because the storage modulus was higher than the loss modulus, all of the 2-, 4- and 8-arm-PEG (POG)$_{10}$ were shown to form gel. The results also suggest that 2-, 4- or 8-arm-PEG-(POG)$_{10}$ forms triple helix with collagen molecules, resulting in crosslinking collagen molecules with each other.

Example 4

Confirmation of the Crosslinking Effects of Collagen Gel by the Crosslinking Agent According to the Present Invention 100 mg of porcine skin-derived type-I atelocollagen (manufactured by Nippon Meat Packers, Inc.) was dissolved in 1 ml of acetate buffer solution. The solution was mixed with 100 µl of acetatebuffer solution containing 4 mg of WSC and 2 mg of N-hydroxy succinimide (NHS) dissolved therein, and the resulting solution was fed dropwise onto a glass plate surface, the droplet was surrounded by silicone rubber spacer having a thickness of 300 µm and covered with another glass plate, and allowed to react at 25° C. for 24 hours, to give a collagen gel.

Figure 3A:
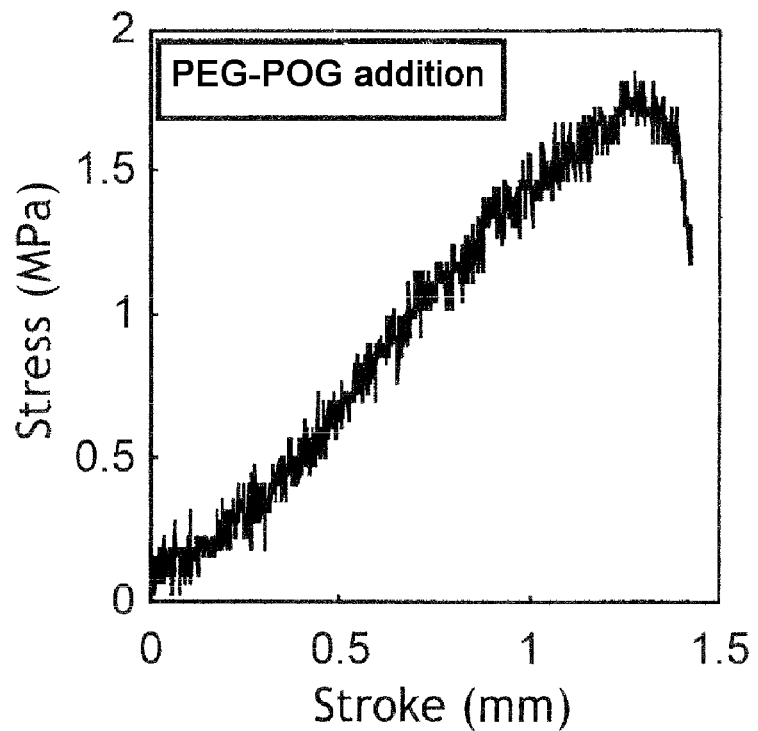
FIG. 3A is a graph showing breaking strength of a collagen disk gel (cornea model) when aqueous crosslinking agent solution according to the present invention is added thereto for crosslinking.

The gel obtained was immersed in phosphate-buffered physiological saline (PBS) overnight, to be washed. The gel was then cut out with a punch having a diameter of 1.6 cm, to give a collagen disk gel having a diameter of 1.6 cm and a thickness of 300 µm. 20 mg of the 4-arm-PEG-(POG)$_{10}$ (Run No. 2 in Table 1) was dissolved in 100 µl of PBS, and the solution was fed dropwise on the disk gel surface and incubated at 4° C. for 12 hours. After incubation, the disk gel was immersed in PBS to be washed, and the breaking strength thereof was measured in a puncture test by using an EZ test small tabletop tester (manufactured by Shimadzu Corporation). Results are shown in FIG. 3A.

Figure 3B:
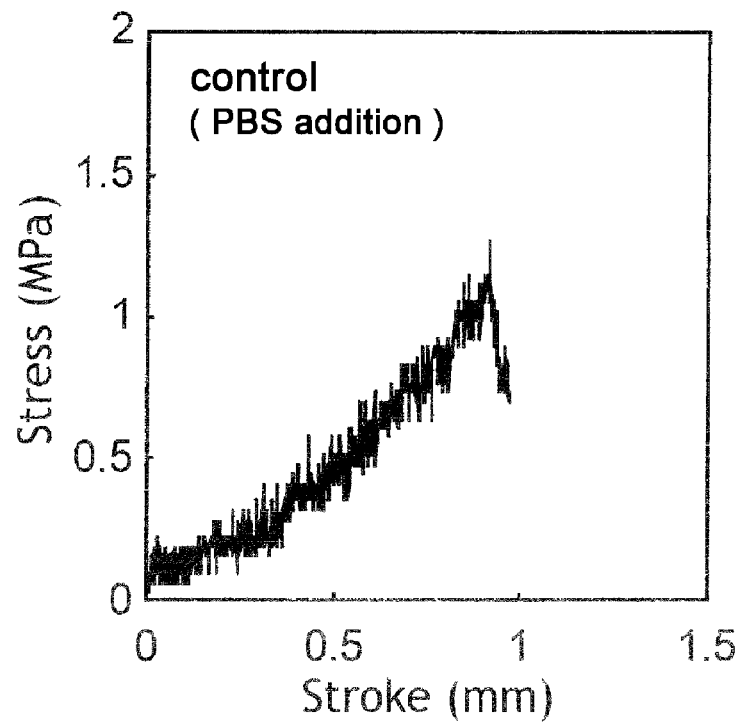
FIG. 3B is a graph showing breaking strength of a collagen disk gel (model cornea) when only the same amount of phosphate-buffered physiological saline (PBS) was added thereto for comparison.
Figure 3C:
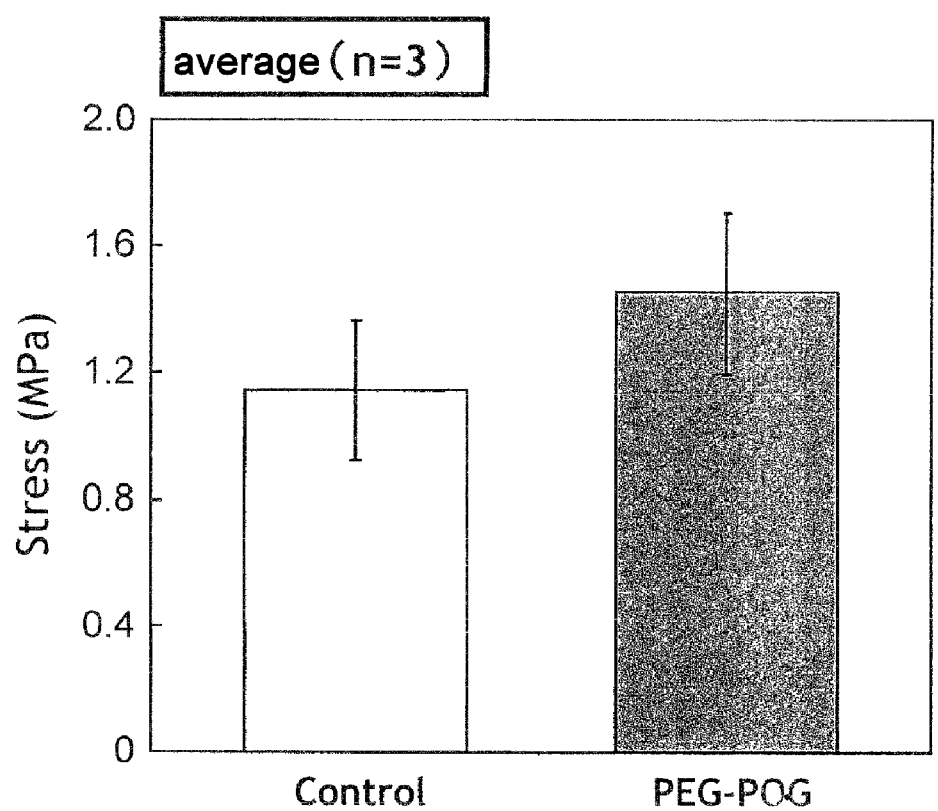
FIG. 3C is a graph comparing breaking strengths of collagen disk gels (average of three measurements) when a crosslinking agent according to the present invention was added and not added thereto.

FIG. 3B shows the results of breaking strength obtained after incubation under the same conditions, except that only PBS in an amount of 100 µl was added dropwise instead of the crosslinking agent. FIG. 3C is a bar chart showing the results of average breaking strength obtained in three tests.

It was confirmed that addition of the crosslinking agent lead to increase in breaking strength. It is known that the parenchymal layer of biogenic cornea is made of type-I collagen and that the parenchymal layer becomes thin and weak, resulting in such a disease as conical cornea. When the crosslinking agent according to the present invention is dropped onto the eyes, it is expected that the parenchymal layer of cornea is strengthened and to have a therapeutic effect to a diseases of the parenchymal layer.

Example 5

Adsorption of Crosslinking Agent onto a Corneoscleral Piece of Rabbit

A fluorescence labeling agent Alexa488 (produced by Invitrogen Corporation) was bound to the 4-arm-PEG-(POG)$_{10}$ (Run No. 2 in Table 1) in condensation reaction by using WSC and NHS, to give a fluorescent-labeled crosslinking agent. 1 mg of the crosslinking agent was dissolved in 1 ml of PBS and the mixture was dropped on the corneoscleral piece of the rabbit and incubated at room temperature for 24 hours. After washed with PBS, the cell nucleus was stained with Hoechst. Observation under fluorescence microscope showed strong fluorescence on one face of the corneal parenchymal layer, indicating that fluorescent-labeled crosslinking agent was adsorbed on the cornea.

INDUSTRIAL APPLICABILITY

The crosslinking agent according to the present invention is useful as a biogenic crosslinking agent, in particular as a collagen crosslinking agent, and the crosslinking agent according to the present invention can be used for gelation of collagen solution and reinforcement of the intensity of collagen gel by using the characteristics described above. The crosslinking agent according to the present invention is also be applicable, for example, for treatment of conical cornea. It is also applicable as a tissue adhesive, in addition to application to the ophthalmic field, and thus may be used in general surgical operations. For that reason, the present invention has a large economical effects and also a large repercussion effects.

The invention claimed is:

1. A noncovalent collagen crosslinking agent, comprising:
a spacer of a polyvalent alcohol having two or more OH groups at terminals and arms of collagen peptides formed of repetitions of three amino acids, wherein
i) the arms are formed of repetitions of three amino acids, and are covalently bound to the polyvalent alcohol via the OH groups,
ii) the arms have the formula (Y—X-G)n, wherein X and Y each independently represent an amino acid residue selected from the group consisting of alanine (Ala), proline (Pro), hydroxyproline (Hyp) and glycine (Gly), G is glycine and n is 1 to 50, and
iii) the arms form triple helices with collagen molecules, thereby crosslinking the collagen.

2. The noncovalent collagen crosslinking agent according to claim 1, wherein the polyvalent alcohol has 3 to 16 OH groups.

3. The noncovalent collagen crosslinking agent according to claim 1, wherein the polyvalent alcohol has four OH groups.

4. The noncovalent collagen crosslinking agent according to claim 1, wherein the polyvalent alcohol is a tetravalent alcohol of pentaerythritol tetrapolyethylene glycol ether or an octavalent alcohol of hexaglycerol octapolyethylene glycol ether.

5. The noncovalent collagen crosslinking agent according to claim 1, wherein the arm is represented by (P—O-G), wherein P is proline, O is hydroxyproline, and G is glycine.

6. The noncovalent collagen crosslinking agent according to claim 1, wherein the arms are represented by the following General Formula (I):

(P—O-G)*n*     (I)

wherein, G represents glycine (Gly) residue; P represents proline (Pro) residue and O represents hydroxyproline (Hyp) residue; and n is an integer of 1 to 50 , and wherein the arms are bound to the spacer of the polyvalent alcohol, which is a tetravalent alcohol of pentaerythritol tetrapolyethylene glycol ether or an octavalent alcohol of hexaglycerol octapolyethylene glycol ether.

7. A noncovalent collagen crosslinking agent, comprising:
a spacer of gold particle and arms of a collagen peptide or a collage model peptide constituted repetitions of three amino acids,
wherein the arms have the formula (Y—X-G)n, wherein Y is cysteine and an Au—S bond is formed between the cysteine and the gold particle, X is Ala, Pro, or Hyp, G is glycine and n is 1 to 50.